Figure 1:
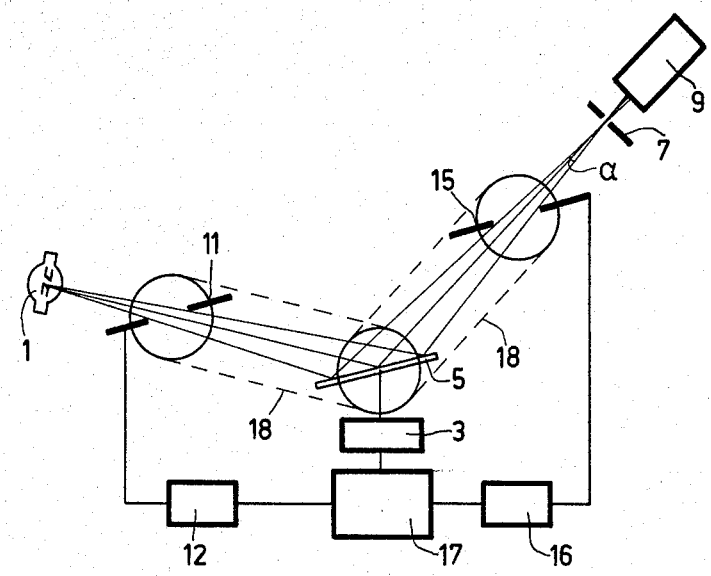

United States Patent [19]

Brandt

[11] Patent Number: 4,535,469
[45] Date of Patent: Aug. 13, 1985

[54] X-RAY ANALYSIS APPARATUS HAVING AN ADJUSTABLE STRAY RADIATION SLIT

[75] Inventor: Cornelis G. Brandt, Almelo, Netherlands

[73] Assignee: U.S. Philips Corporation, New York, N.Y.

[21] Appl. No.: 477,279

[22] Filed: Mar. 21, 1983

[30] Foreign Application Priority Data

Mar. 31, 1982 [NL] Netherlands .......................... 8201343

[51] Int. Cl.³ ............................................. G01N 23/20
[52] U.S. Cl. ..................................... 378/081; 378/153
[58] Field of Search .................. 378/79, 81, 73, 78, 378/153

[56] References Cited

U.S. PATENT DOCUMENTS

| | | | |
|---|---|---|---|
| 2,870,337 | 1/1959 | Neff | 378/81 |
| 3,411,000 | 11/1968 | Schliephake et al. | 378/153 |
| 3,852,594 | 12/1974 | Paolini | 378/81 |
| 3,855,469 | 12/1974 | Pluchery et al. | 378/79 |
| 4,412,345 | 10/1983 | Workman et al. | 378/78 |

*Primary Examiner*—Alfred E. Smith
*Assistant Examiner*—T. N. Grigsby
*Attorney, Agent, or Firm*—Paul R. Miller

[57] ABSTRACT

In an X-ray analysis apparatus, there is provided between a test specimen (5) or an analyzing crystal and a detector (9) a stray radiation slit (15) that can be adjusted in dependence on the goniometer angle. By an optimum adjustment of this slit in correspondence with the variation in the goniometer angle it can be achieved that the detector will always see the same portion of the surface of the test sample or analyzing crystal. Especially, the adjustment of the slit is coupled to the adjustment of an automatic divergence slit (11) so that the portion of the surface which is irradiated, remains unaltered. Especially for small goniometer angles, that is to say for the analysis of a substance in which there is a large distance between crystal planes, a considerably improved signal-to-noise ratio in the measurement signal is thus obtained.

10 Claims, 2 Drawing Figures

X-RAY ANALYSIS APPARATUS HAVING AN ADJUSTABLE STRAY RADIATION SLIT

The invention relates to an X-ray analysis apparatus including an X-ray source, a goniometer with an angle-adjusting mechanism and an X-ray detector.

Such an X-ray analysis apparatus in the form of an X-ray diffractometer is known from U.S. Pat. No. 3,852,594. The apparatus described therein comprises a goniometer with an angle-adjusting mechanism for orienting a test sample, to which an angular adjustment for an entrance slit for the X-ray beam, sometimes called a divergence slit, is coupled so that the same portion of the surface of the sample is irradiated throughout a range of incidence angles to be used during a measurement.

In such an apparatus, especially at smaller angles of incidence, a detrimental effect is produced by background radiation, as a result of which the signal-to-noise ratio of the measurement is adversely affected.

The invention has for its object to provide an X-ray analysis apparatus, in which, especially for the range of smaller angles of incidence, an improvement in the signal-to-noise ratio of the measurement signal is effected. According to the invention, an X-ray analysis apparatus of the kind mentioned in the opening paragraph is therefore characterized in that between the goniometer and the detector there is provided a stray radiation slit that can be adjusted in correspondence with the angular adjustment of the goniometer. Here and hereinafter a goniometer is assumed to be an angle-adjusting mechanism either for the sample stage of an X-ray diffractometer or for the analysing crystal of an X-ray crystal spectrometer.

By adjusting the stray radiation slit in accordance with the adjustment of the divergence slit it can be achieved that the detector will always see substantially the same part of the surface of the test sample through the stray radiation slit throughout the entire range of angles of incidence. In a practical construction, this part of the surface will be adjusted to correspond to that part of the surface which is directly irradiated. At smaller values of the incidence angle, consequently a considerably smaller amount of the surface will be seen than with a fixed slit which will be adjusted so that at large angles of incidence the whole of the irradiated part of the surface can be seen. Consequently, especially at smaller angles of incidence, a considerable improvement in the signal-to-noise ratio of the measurement signal is provided, as a result of which especially in this operational region, measurements can be made with greater accuracy and with greater sensitivity.

In a preferred embodiment according to the invention, an adjustment mechanism for the goniometer ensures directly by means of a mechanical coupling, an angular adjustment of the stray radiation slit and preferably also directly an angular adjustment of the divergence slit. As a result, an optimum signal-to-noise ratio is attained for each value of the incidence angle. The coupling mechanism can then be constructed in accordance with the mechanism described in U.S. Pat. No. 3,852,594 and which could take the form of a dual mechanism. In an X-ray diffractometer, it is favourable to arrange the two slits at about the same distance from the sample. The slits and the adjustment mechanisms for the two slits can then be made to have substantially the same form of construction.

In a further preferred embodiment, both adjustments are correlated with the angular adjustment of the goniometer controlled from the central control unit. The advantage is then obtained that it is possible to depart from the geometrically fixed proportions. For a given range of incidence angles, for example, a greater or a lesser improvement can be provided with respect to other ranges. For example, the effective slit width of the stray radiation slit may be varied non-linearly with the effective slit width of the divergence slit. For desired ranges, for example, the noise can then be reduced to an even greater extent, albeit at the expense of some signal strength, or the dynamic range of the output signal can be reduced.

Figure 2:
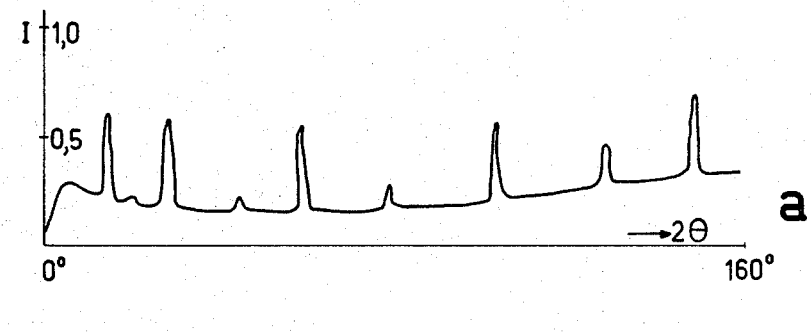
Figure 2:
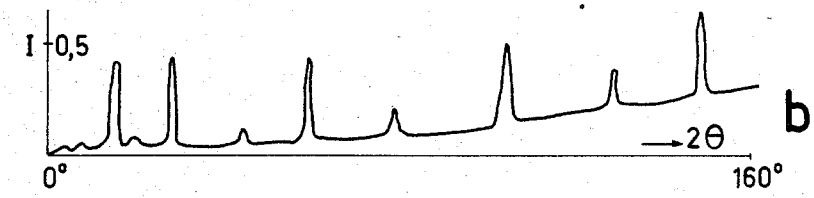

A few preferred embodiments of the invention will be described more fully hereinafter with reference to the drawing. In the drawing:

FIG. 1 is a schematic representation of the relative positioning of the source, slits, test sample and detector of an X-ray diffractometer according to the invention; and FIG. 2 shows for comparison measurement results obtained by means of apparatus including apparatus according to the invention.

Referring to a diffractometer according to the invention, FIG. 1 shows an X-ray source 1, a test sample 5 arranged with a goniometer 3 and a detector 9 provided with a detector slit 7. Between the source 1 and the sample 5 there is located a rotatable divergence slit 11 with an adjusting mechanism 12. As described in U.S. Pat. No. 3,852,594, the rotation of this slit is made to correspond with the rotation of the test sample which is to be carried out by means of the goniometer for measurement purposes. Thus, it is achieved that an X-ray beam 13 emitted by the source will irradiate the same amount of the surface of the test sample even when the goniometer angle $\theta$ is varied. Between the test sample and the detector slit 7 there is present in known diffractometers a fixed stray radiation slit not shown in the Figures. This slit determines for the detector an aperture angle $\alpha$, as a result of which for each goniometer angle at least the whole of the irradiated portion of the surface of the test sample will remain visible. The width of the slit is then chosen in the usual manner so that at large goniometer angles the, then apparently extensive, irradiated surface of the test sample is seen by the detector. At decreasing values of the goniometer angle $\theta$, a gradually increasing part of the remainder of the surface of the test sample will become visible to the detector in addition to the directly irradiated portion of the surface. As a result, a comparatively large quantity of stray radiation can reach the detector, which will adversely affect the signal-to-noise ratio in the measurement signal. When in this arrangement the stray radiation slit is also made adjustable, which in principle limits the angular aperture, and which for all values of the goniometer angle $\theta$ makes visible to the detector only the directly irradiated portion of the surface, a considerable improvement is obtained. A stray radiation slit 15, which according to the invention is provided with an adjusting mechanism 16, may be adjusted, for example, completely in accordance with the arrangement used to adjust the divergence slit 11 in the known apparatus. Starting from the angular displacement means of the goniometer, the two slits are then adjusted synchronously by means of the direct mechanical coupling 18. This adjustment need not be a rotation, but may alternatively be provided by opening the slits to a greater or lesser extent or, albeit rather less conveniently, by displacing the slits along the direction of the main ray of the X-ray beam. If the two adjustments are not to be coupled directly in operation, both slits can be adjusted in correspondence with the goniometer adjustment from a central control unit 17 according to a selected program. In order to reduce the dynamic range in the signal to be detected, a small variation in the irradiated amount of the surface of the test sample can be effected for this purpose.

The position of the stray radiation slit 15 can be chosen almost at will. The advantage of making the distances from the test sample to the divergence slit 11 and to the stray radiation slit 15 the same, has already been pointed out. A position of the stray radiation slit close to the test sample would result in a greater margin of adjustment due to the fact that the width of the beam is greater there. A position close to the detector, in which case an alternative position between the detector slit and the detector would be permissible, can result in better screening from stray radiation, but would require more accurate adjustment. Corresponding considerations apply to the positioning of a stray radiation slit with respect to an analysing crystal in an X-ray spectrometer.

In FIG. 2, the relative intensity I as a function of the goniometer angle $2\theta$ is shown by a graph. Measurement results from an apparatus according to the prior art are represented by a curve a and measurement results from an apparatus according to the invention are represented by a curve b, both curves being drawn, of source, to the same scale.

Especially for goniometer angles $2\theta$ up to about 60°, the advantage will be clearly apparent. As a result, the analysis of test samples, especially of substances having a comparatively large d-value, that is to say a large relative distance between crystal planes, has become considerably more accurate whereas the mere presence of these very substances could only be indicated by other prior methods with comparatively great difficulty due to the low signal-to-noise ratio that can be attained in analysis thereby.

What is claimed is:

1. An X-ray analysis apparatus comprising an X-ray source,
   a goniometer for mounting a specimen which receives radiation from said X-ray source, said goniometer having an angle adjusting mechanism,
   a stray radiation slit controlling said radiation from said specimen, the effective width of said stray radiation slit being adjustable in correspondence with said angular adjustment of said goniometer,
   a detector slit receiving said radiation from said stray radiation slit, and
   an X-ray detector receiving said radiation from said detector slit,
   wherein signal-to-noise ratios of analysis measurements are significantly improved.

2. An X-ray analysis apparatus according to claim 1, wherein said stray radiation slit includes an angular adjustment mechanism for rotatably opening or closing widths of said slit, said angular adjustment mechanism of said stray radiation slit being mechanically coupled to said angular adjustment of said goniometer.

3. An X-ray analysis apparatus according to claim 2, further comprising a diffraction apparatus, wherein a central control unit ensures that said stray radiation slit is rotatably adjusted in correspondence with angular adjustment of said goniometer.

4. An X-ray analysis apparatus according to claim 3, wherein said central control unit ensures angular adjustment of a rotatable divergence slit receiving radiation from said source and passing said radiation to said specimen, said angular adjustment of said rotatable divergence slit corresponding to angular adjustment of said goniometer.

5. An X-ray analysis apparatus according to claim 4, wherein said rotatable divergence slit is approximately at the same distance from said specimen as said stray radiation slit is from said specimen.

6. An X-ray analysis apparatus according to claim 4, wherein said stray radiation slit has an effective slit width which is varied non-linearly by said central control unit with respect to an effective slit width of said rotatable divergence slit.

7. An X-ray analysis apparatus according to claim 1, wherein a rotatable divergence slit receives said radiation from said X-ray source and passes said radiation to said specimen, said rotatable divergence slit including an angular adjustment mechanism being mechanically coupled by said angle adjustment mechanism of said goniometer to an angular adjustment mechanism of said stray radiation slit.

8. An X-ray analysis apparatus according to claim 7, wherein said rotatable divergence slit is approximately at the same distance from said specimen as said stray radiation slit is from said specimen.

9. An X-ray analysis apparatus according to claim 7, further comprising a diffraction apparatus, wherein said angular adjustment mechanism for said goniometer and for said slits ensure synchronously effected angular adjustments for said goniometer and said slits.

10. An X-ray analysis apparatus according to one of claim 4 or claim 7 or claim 9, wherein said stray radiation slit has a slit opening mutually coupled in an adjustable manner to a slit opening of said rotatable divergence slit.

* * * * *